United States Patent
Vicatos et al.

(10) Patent No.: US 9,867,638 B2
(45) Date of Patent: Jan. 16, 2018

(54) TRANSPORT DISTRACTION APPARATUS

(71) Applicant: University of Cape Town, Cape Town (ZA)

(72) Inventors: George Vicatos, Cape Town (ZA); Mogamat Rushdie Hendriks, Cape Town (ZA); James Angus Boonzaier, Cape Town (ZA)

(73) Assignee: University of Cape Town, Cape Town (ZA)

( * ) Notice: Subject to any disclaimer, the term of this patent is extended or adjusted under 35 U.S.C. 154(b) by 28 days.

(21) Appl. No.: 14/360,560

(22) PCT Filed: Nov. 23, 2012

(86) PCT No.: PCT/IB2012/056664
§ 371 (c)(1),
(2) Date: May 23, 2014

(87) PCT Pub. No.: WO2013/076693
PCT Pub. Date: May 30, 2013

(65) Prior Publication Data
US 2014/0324046 A1    Oct. 30, 2014

(30) Foreign Application Priority Data
Nov. 25, 2011   (ZA) ................................ 2011/08678

(51) Int. Cl.
*A61B 17/66*   (2006.01)

(52) U.S. Cl.
CPC ................................ *A61B 17/663* (2013.01)

(58) Field of Classification Search
CPC ............ A61B 17/7081; A61B 17/8004; A61B 17/663–17/666; Y10S 606/903–606/904
See application file for complete search history.

(56) References Cited

U.S. PATENT DOCUMENTS 5,700,263 A    12/1997  Schendel
5,855,580 A *   1/1999  Kreidler et al. ................ 606/71
(Continued)

FOREIGN PATENT DOCUMENTS

CH           693557 A5    10/2003
FR         2954904 A1     7/2011
(Continued)

OTHER PUBLICATIONS

International Search Report dated Mar. 27, 2013 relating to International Application No. PCT/162012/056664.

*Primary Examiner* — Jacqueline Johanas
(74) *Attorney, Agent, or Firm* — Honigman Miller Schwartz and Cohn LLP (57) ABSTRACT

Transport distraction apparatus for performing transport distraction osteogenesis is provided which includes a track capable of being formed into a curvilinear shape with a carriage movable longitudinally along the track. The carriage has a fixation plate secured or securable to it and at least one gear for moving the carriage along the track in order to adjust its position relative to the length of the track. The track has a series of formations extending along one edge of the track and engaged by the gear which is at least partially accommodated within a space between a plane including the front face of the track and a plane including the rear face of the track. Preferably, the apparatus creates a gap between a central region of the track and a patient's bone in use. A fixation plate is also provided.

11 Claims, 6 Drawing Sheets

(56) References Cited

U.S. PATENT DOCUMENTS

| | | | |
|---|---|---|---|
| 5,902,304 A * | 5/1999 | Walker et al. .................. 606/71 |
| 6,139,316 A * | 10/2000 | Sachdeva ............. A61B 17/663 |
| | | | 433/7 |
| 6,350,265 B1 * | 2/2002 | Blaustein ........... A61B 17/8071 |
| | | | 606/300 |
| 6,972,020 B1 * | 12/2005 | Grayson et al. ................ 606/90 |
| 7,182,785 B2 * | 2/2007 | Elsalanty et al. .......... 623/17.17 |
| 7,601,175 B2 * | 10/2009 | Feigenwinter ..... A61B 17/8071 |
| | | | 623/17.17 |
| 7,998,216 B2 * | 8/2011 | Elsalanty et al. .......... 623/17.17 |
| 8,287,573 B2 * | 10/2012 | Mulone .......................... 606/282 |
| 8,808,290 B2 * | 8/2014 | Dubois ........................... 606/58 |
| 2002/0062127 A1 * | 5/2002 | Schumacher ...... A61B 17/8047 |
| | | | 606/70 |
| 2003/0105463 A1 * | 6/2003 | Wolgen ................ A61B 17/663 |
| | | | 606/71 |
| 2005/0119659 A1 | 6/2005 | Pfefferle et al. |
| 2005/0203628 A1 * | 9/2005 | Elsalanty et al. .......... 623/17.17 |
| 2006/0122606 A1 * | 6/2006 | Wolgen ................ A61B 17/663 |
| | | | 606/71 |
| 2007/0043370 A1 | 2/2007 | Ueda et al. |
| 2007/0162045 A1 | 7/2007 | Ahmad |
| 2007/0276502 A1 * | 11/2007 | Elsalanty et al. .......... 623/17.17 |
| 2008/0311542 A1 * | 12/2008 | Rana .................... A61B 17/663 |
| | | | 433/140 |
| 2010/0152734 A1 * | 6/2010 | Mulone ........................... 606/60 |
| 2011/0125162 A1 * | 5/2011 | Noon et al. ................... 606/105 |
| 2012/0316561 A1 * | 12/2012 | Dubois ........................... 606/58 |
| 2016/0058485 A1 * | 3/2016 | Staehler ............. A61B 17/8004 |
| | | | 606/282 |

FOREIGN PATENT DOCUMENTS

| | | |
|---|---|---|
| JP | 11262491 | 9/1999 |
| WO | WO-1996035391 A1 | 11/1996 |
| WO | WO-2004002341 A1 | 1/2004 |

* cited by examiner

TRANSPORT DISTRACTION APPARATUS

FIELD OF THE INVENTION

This invention relates to apparatus for use in transport distraction osteogenesis, more particularly, but not exclusively, to osteogenesis for the reconstruction of the human maxilla.

BACKGROUND TO THE INVENTION

Transport distraction osteogenesis (TDO) was pioneered at the turn of the 20th century. It was originally applied as a method of leg lengthening to correct discrepancies between legs. As such, its early development was in the area of orthopaedics. The concepts have since been adapted to maxillofacial reconstructive surgery. Transport distraction osteogenesis is now commonly applied to regeneration of the maxilla and mandible where they are absent as well as the correction of various facial bone abnormalities.

Transport distraction osteogenesis involves surgical fracture of the bone, a latent period to facilitate initial healing of the fracture, and then incremental, relative distraction of the fracture surfaces. The relative displacement of the fracture surfaces facilitates the generation of new bone at the interface. By incrementally distracting the healing fracture surfaces at a rate of approximately 1 mm per day, it is possible to gradually extend existing bone segments or generate sections of entirely new bone where deficiencies are present.

During Transport Distraction Osteogenesis, distraction is mechanically controlled and, as such, the mechanical stability and control of the healing environment is crucial to the resultant physical properties of the generated bone and thus the success of the procedure.

The most common abnormalities of the maxillofacial region are congenital defects, bone disease or the result of surgical removal of tumours. The effects of these disorders include total discontinuity of the maxilla or mandible, and the total or partial absence of the alveolar ridge. Such defects have serious implications for the quality of life of patients after reconstructive surgery as the maxilla and mandible are responsible for the crucial functions of chewing, swallowing, speaking and facial expression.

Transport distraction osteogenesis offers numerous benefits over other facial reconstruction techniques such as bone grafting. The benefits of transport distraction osteogenesis include reduced patient trauma and faster patient recovery. It also eliminates the associated risks of bone grafting such as rejection of the graft/implant by the human body. The major benefit, however, is that transport distraction osteogenesis regenerates not only the structural bone, but also the surrounding soft tissue and blood supply. In the case of grafting, a prolonged period of healing is required before these are restored.

Reconstruction of large maxillectomy defects following tumour resection presents a formidable challenge to both surgeons and prosthodontists. In addition to the hermetic obturation of the large oro-nasal-antral defects, successful rehabilitation has to take into account the demands of aesthetics, function, deglutition and speech. To this end, it would be desirable to re-create a functional palatal vault, alveolar ridge that can house dental-implants and a vestibule for supportive form and function of cheeks. Due to the large size and complexity of various maxillectomy defects, the structural and functional restoration requires composite tissue replacement involving free vascularized flaps harvested from the tibia or fibula. These procedures demand long and skillful surgical techniques and, though often highly successful, are not always predictable and cause significant donor site morbidity.

Various transport distractors have been developed by companies such as KLS Martin and BIOMET Microfixation. However, most existing maxillofacial transport distractors are not practically suited to distraction in the anterior curved segment of the maxilla. These devices are uncomfortably large and do not perform well on curvilinear trajectories.

Titanium fixation plating systems are widely used in maxillo-facial reconstruction. They are used to create a structural connection between bone anatomies that require support. In addition, titanium plating systems can be used to form a rigid rail for guiding distraction, hereinafter referred to as the 'trajectory rail', for transport distractors.

Some distractors are capable of following curvilinear trajectories, but the nature of the designs makes them inappropriate for distraction along curves such as those present in the anterior segments of the mandible and maxilla. This problem has been partially resolved by approximating the desired curve with multiple linear distractions or the use of multiple distractors simultaneously. This is known as bifocal distraction. However, it has been found that a two-stage mandibular distraction requires four invasive operations whilst the generated geometry is not true to the ideal form of the mandible.

Due to the complex anatomical constraints of the maxilla, currently available distractors cannot deal with the demands of the upper jaw and at present there are no transport distractors available for anterior to posterior distraction in the maxilla.

United States published patent application US20100152734 describes a proposed device in which a carriage that can be secured to one part of the maxilla or mandible, as the case may be, and a track having a series of transverse grooves therein that cooperate with a worm gear to move the carriage along the track incrementally as required in a transport distraction osteogenesis procedure. However, the device proposed is rather thick in that it requires appreciable space in the direction at right angles to the maxilla or mandible thereby contributing significantly to patient discomfort by protruding and becoming obtrusive inside the patient's mouth. The device described also has a carriage that is detachable from bracket flanges thereby complicating the mechanism further and making it more bulky. The driver of the worm gear and the position of the worm gear allow the device to be accessed only as long as there is available space in the patient's mouth and as long the device is placed on the mandible. Considering the anatomical variations and inaccessible spaces of the maxilla, this device besides being cumbersome, is inappropriate to provide traction, especially as the demands may dictate, such as from the right side through the front to the left and to the back of the maxilla. Also in the maxilla, a three dimensional curvilinear traction may be necessary and the device described may not be able to provide locomotion on a spiral.

SUMMARY OF THE INVENTION

In accordance of a first aspect of the invention there is provided transport distraction apparatus for performing transport distraction osteogenesis which includes a track having a width greater than its thickness to provide a front and a rear face and two longitudinally extending edges and wherein the track is capable of being formed into a curvilinear shape, a carriage movable longitudinally along the track and to which a fixation plate is secured or is securable, and at least one gear for moving the carriage along the track in order to adjust its position relative to the length of the track, the apparatus being characterized in that the track has a series of formations extending along one edge of the track such that at least one gear is at least partially accommodated within a space between a plane including the front face of the track and a plane including the rear face of the track and wherein the track itself is releasably secured by fasteners to a separate elongate mounting that is securable by fasteners to bone in a patient such that removal may take place in a direction that is transverse to the length of the track.

Further features of the first aspect of the invention provide for the gear to be a worm gear with a helically extending thread which meshes a toothed rack extending along the said edge of the track; and for the worm gear to have formations at both ends thereof for releasable engagement by a tool for rotating the worm gear and thereby moving the carriage relative to the length of the track.

Still further features of the first aspect of the invention provide for the track, and especially the end regions thereof or a separate elongate mounting, to have a plurality of apertures located generally centrally with respect to the width of the track or mounting and spaced apart along its length; and for the track and where appropriate the separate elongate mounting to be made of a suitable titanium material that is adequately deformable to enable it to be bent to follow a required contour in at least one plane and optionally suitable for being twisted to at least a small extent.

A still further feature of the invention provides for the mounting or shaping of the track to be such that a central region of the track and the attachment or attachment position for the fixation plate to the carriage are spaced forwardly of the separate elongate mounting that is operatively secured to bone in a patient A further feature of the invention provides for the rear face of the central region of the track to be spaced forwardly of the separate elongate mounting that is operatively secured to bone in a patient by a distance of the order of the thickness of the mounting.

A yet further feature of the invention provides for the fixation plate to be a generally flat plate having an attachment formation attaching the plate to the carriage and wherein the fixation plate has deep generally sector shaped cut-out portions extending inwardly towards the attachment formation so as to define plural arms capable of independent bending to conform generally to a three-dimensional curve.

Further features of the fixation plate provide for the fixation plate to be generally semicircular in shape with two, three, or four sector shaped cut-out portions defining a plurality of arms extending in a generally radial direction from the attachment formation; for the fixation plate to be made of a titanium or medical grade stainless steel material; and for each of the arms to be perforated with multiple perforations that can be used for securing the fixation plate in position, in use.

The invention also provides a fixation plate for use in transport distraction apparatus, the fixation plate having an attachment formation for attaching the plate to a carriage of distraction apparatus, the fixation plate having deep generally sector shaped cut-out portions extending inwardly towards the attachment formation so as to define plural arms capable of independent bending to conform generally to a three-dimensional curve.

In order that the above and other features of the invention may be more fully understood, two embodiments of the invention that illustrate each of the different aspects of the invention will now be described with reference to the accompanying drawings.

DETAILED DESCRIPTION WITH REFERENCE TO THE DRAWINGS

Figure 15:
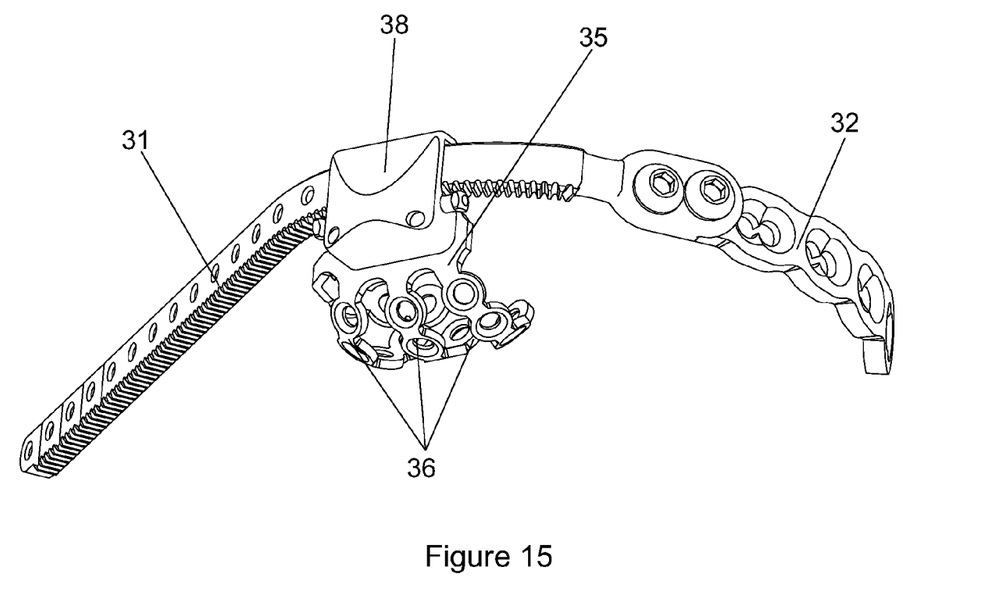

As illustrated in FIGS. 1 to 7 of the accompanying drawings, one embodiment of transport distraction apparatus (1) according to the invention, hereinafter referred to as "the distractor", includes a track (2) with a carriage (3) movable along at least a central part of its length wherein the carriage carries a perforated or mesh fixation plate (4). The track (2) is of a type generally known in the art and assumes the form of a titanium strip having a plurality of apertures (5) roughly centrally located with respect to the width of the track and spaced apart along its length. The apertures are suitable for receiving fasteners for securing the track directly to the bone of a patient. The track is such that it may be bent to take on a suitable curvilinear shape in use as shown quite clearly in FIG. 15.

The width of the track is greater than its thickness to provide a front face (6) and a rear face (7) (see FIGS. 2 and 3) with two longitudinally extending edges. In the present embodiment of the invention the width is typically about three times the thickness of the track. The one edge of the track has a toothed rack (8) extending along its length.

The carriage (3) is movable longitudinally along at least the central region of the track and carries the fixation plate (4) that is made as a separate component that easily attaches to the carriage. As shown most clearly in FIGS. 2 and 6, the carriage comprises a body part (12) having a recess (13) for accommodating the track and a rotatable worm gear (14) having the usual helically extending thread wherein the worm gear extends parallel to the track and engages the toothed rack that extends along the one edge of the track. Each end of the worm gear extends out of the body part of the carriage and is formed into a polygonal shaped head (15) for engagement by a socket carried by a tool (not shown).

Figures 1, 2, 4:
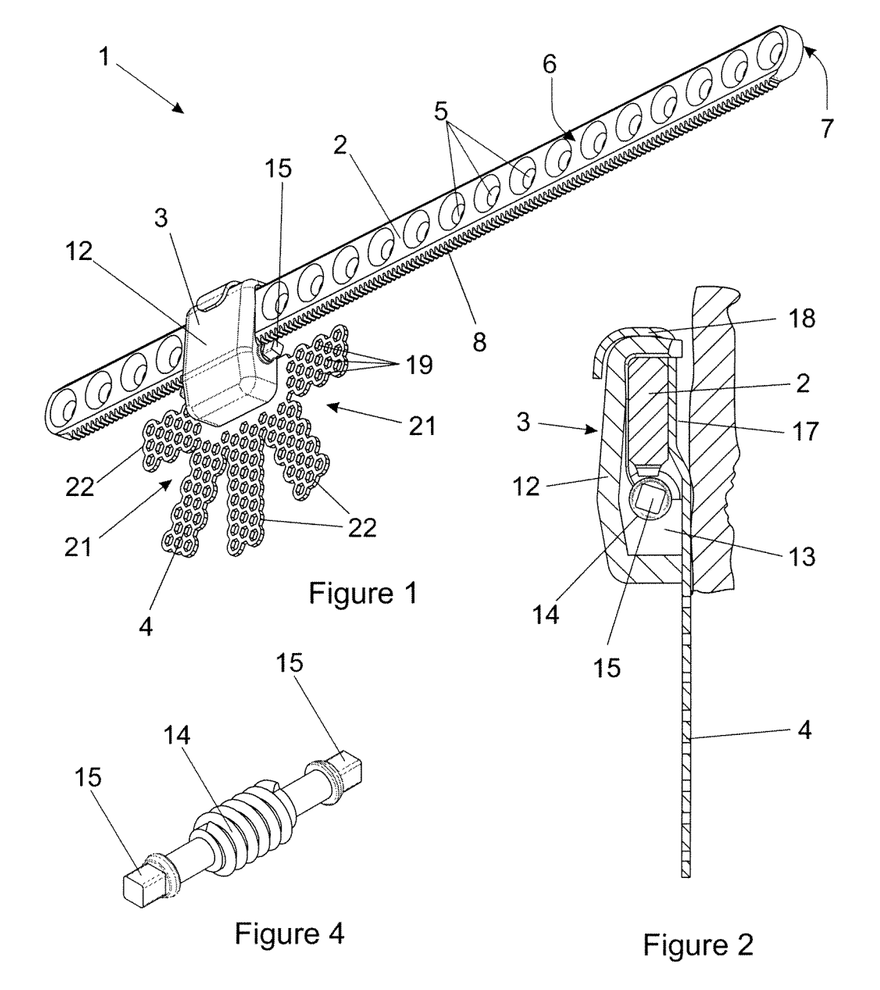
FIG. 1 is a perspective view of one embodiment of transport distraction apparatus according to the invention.
FIG. 2 is a cross-section taken through the track and carriage of the apparatus illustrated in FIG. 1.
FIG. 4 is a perspective view of a worm gear utilised in the apparatus illustrated in FIGS. 1 to 3.
Figure 3:
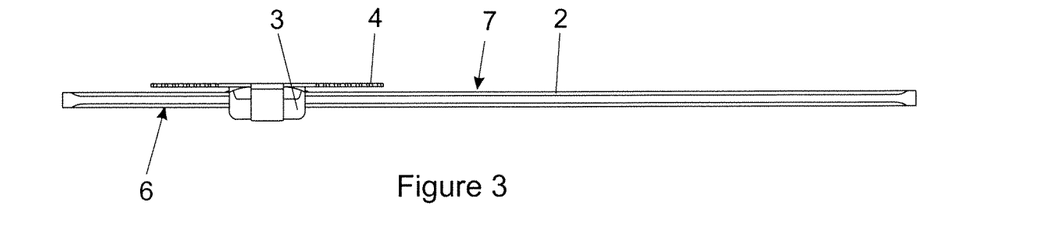
FIG. 3 is a plan view of the apparatus illustrated in FIG. 1.
Figure 5:
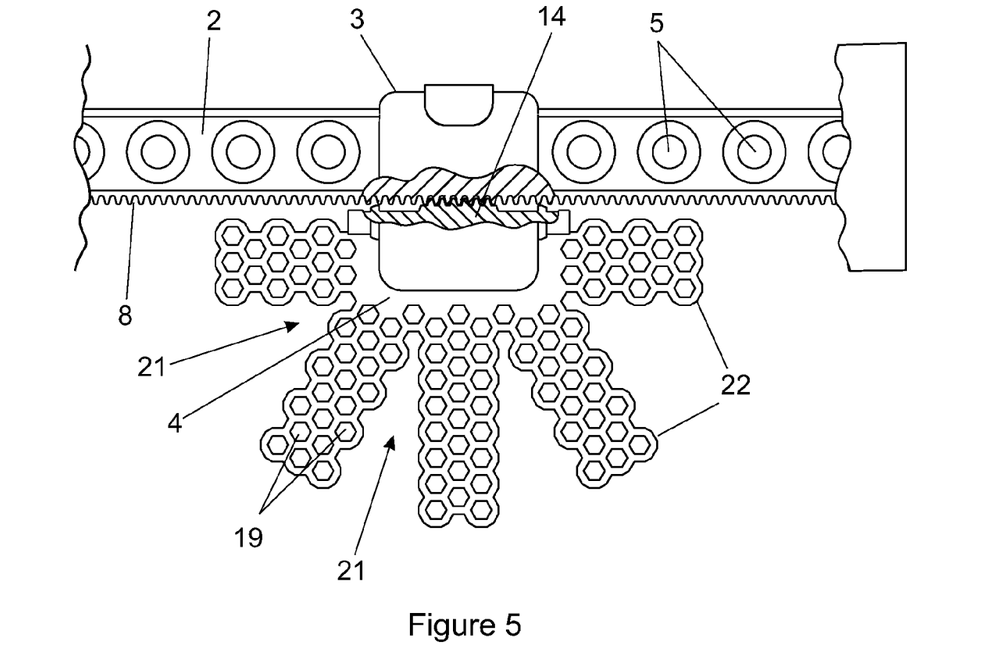
FIG. 5 is an enlarged and partly cut away elevation of the central region of the track and carriage of the apparatus illustrated in FIG. 1.
Figure 6:
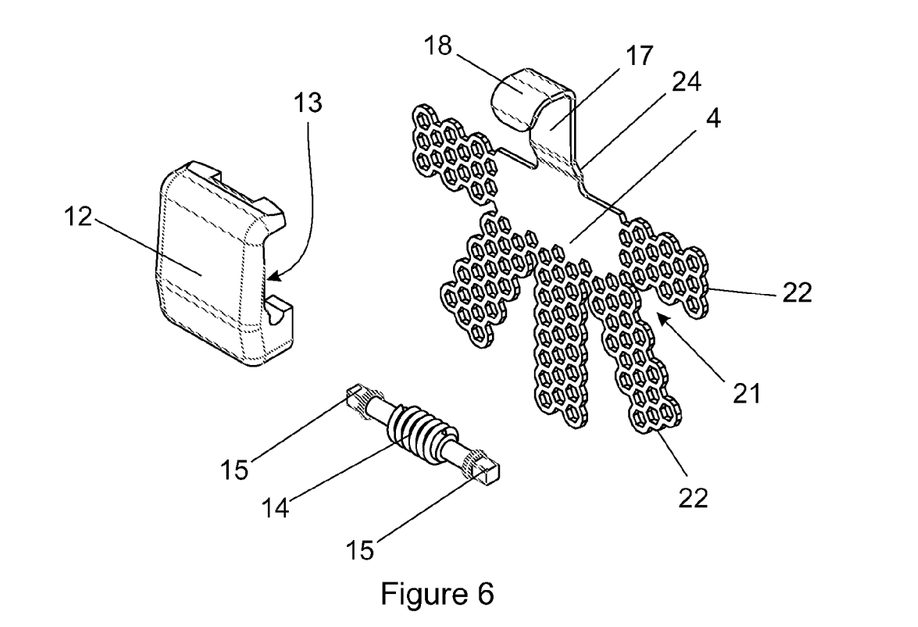
FIG. 6 is an exploded perspective view of the carriage and fixation plate assembly of the apparatus illustrated in FIGS. 1 to 5.

This arrangement enables the worm gear to be engaged from either end, as may be dictated by ease of access, and therefore the carriage can be moved in either direction by rotating the appropriate end of the worm gear in order to adjust the position of the carriage relative to the length of the track.

The construction of the carriage and fixation plate is extremely simple so that assembly is greatly facilitated.

To this end, the fixation plate has an extension (17) terminating in a hook (18) that extends from the part of the fixation plate forming the attachment formation. The hook fits over the outside of one edge of the body part of the carriage and the attachment formation bridges the opening to the recess (13) in the body part to close it. As illustrated in FIG. 2, the extension (17) of the fixation plate (4) is configured to extend between the track and a bone of a patient. The fixation plate is secured to the other side of the recess in the body to thereby hold the worm gear captive in its operative position and the carriage captive relative to the track. This part of the fixation plate thus forms the attachment formation mentioned above.

With this arrangement the worm gear is substantially accommodated within the space between a plane including the front face of the track and a plane including the rear face of the track to provide an extremely low profile carriage with respect to the track.

The fixation plate, as provided by this invention, is a generally flat plate of titanium having a multitude of perforations (19) therethrough with deep, generally sector shaped cut-out portions (21), extending inwardly towards the attachment formation so as to define plural arms (22) capable of being bent independently of each other to conform generally to a three-dimensional curved surface. In this particular instance there are four sector shaped cut-outs so that five generally radially extending arms are provided in a generally semicircular arrangement.

The fixation plate has an angled connection zone (24) interconnecting the two parts of the fixation plate. In this manner the rear face of the central region of the track is spaced forwardly of the rear face of the end regions of the track by a distance that may typically be of the order of 1 mm depending on the thickness of the track. This offset accommodates the difference in thickness of the track and the diameter of the worm gear and would typically be slightly more than half the difference between the track thickness and the diameter of the worm gear.

It is generally possible, although not necessarily convenient, to ensure that the relevant part of the track along which the carriage is to move in a particular instance is adequately spaced from the bone to ensure that the bone does not interfere with movement of the carriage, or, on the other hand, the carriage does not damage the bone. However, it is preferred that the second aspect of the invention be employed to facilitate this.

Figure 7:
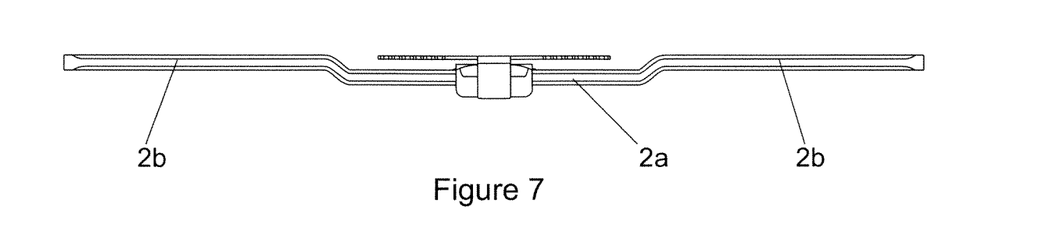
FIG. 7 is a view similar to FIG. 3 but illustrating the incorporation of the second aspect of the invention.

In this instance, as shown most clearly in FIG. 7, the central region (2a) of the track is spaced forwardly of the rear face of the two end regions (2b) of the track such that attachment of said end regions to bone in a patient can more easily be achieved with the central region of the track and the carriage being out of contact with the bone.

In use, detailed measurements of a patient's anatomy may be made and a three dimensional model is preferably constructed, conveniently using rapid prototyping or stereolithographic printing technology. This permits the trajectory of the track (2) to be carefully calculated and the track to be bent into the basically required shape beforehand. It may be necessary to use further fixation plates to secure the track (2) in position and these too can be prepared ahead of time.

In calculating the trajectory of the track (2) it will be taken into consideration that it must be sufficiently spaced from other bones to permit uninhibited movement of the carriage and that it not have unacceptably sharp curves and the construction of the central region of the track described above greatly facilitates this.

Figure 8:
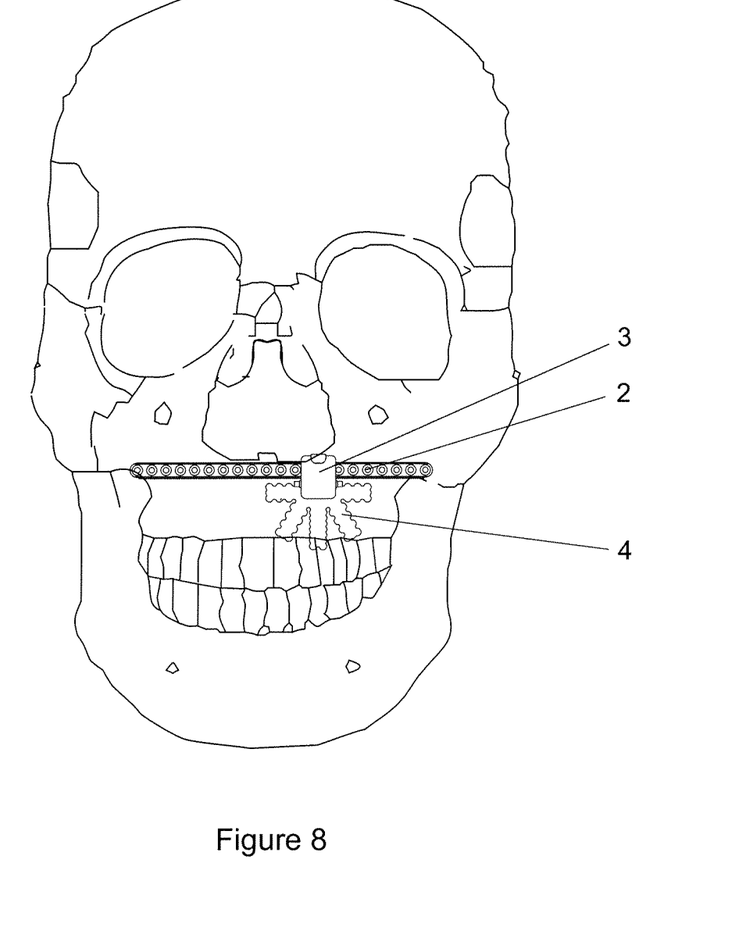
FIG. 8 is an elevation of the apparatus illustrated in FIGS. 1 to 7 showing schematically the application of the apparatus to the maxilla of a human skull.
Figure 9:
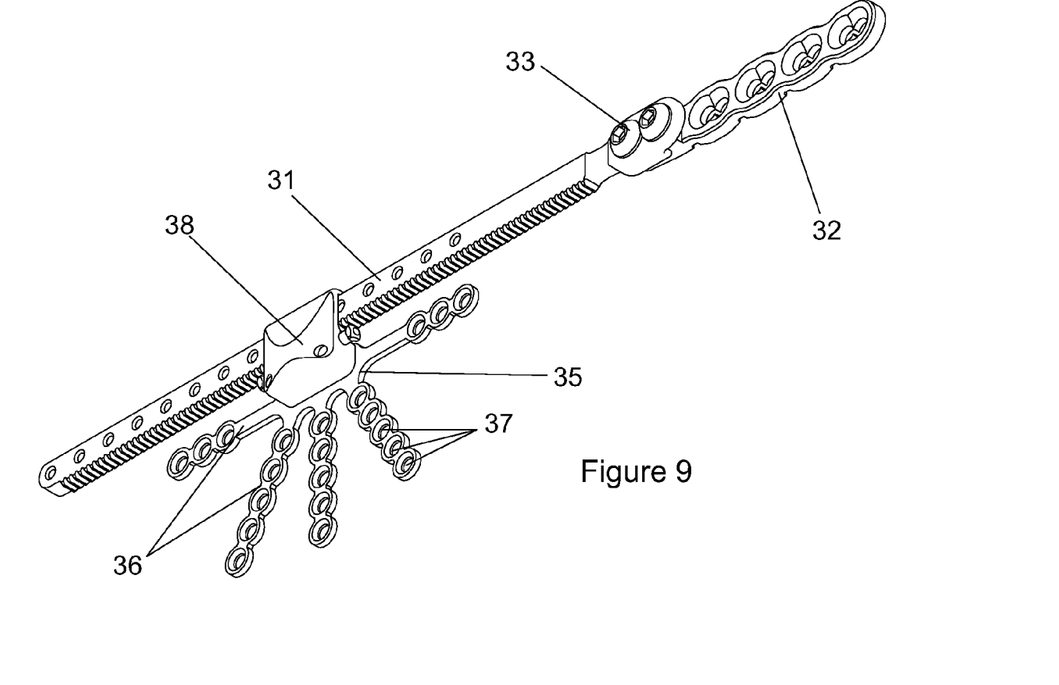
FIG. 9 is a view similar to FIG. 1 blood of a second embodiment of the invention.
Figure 10:
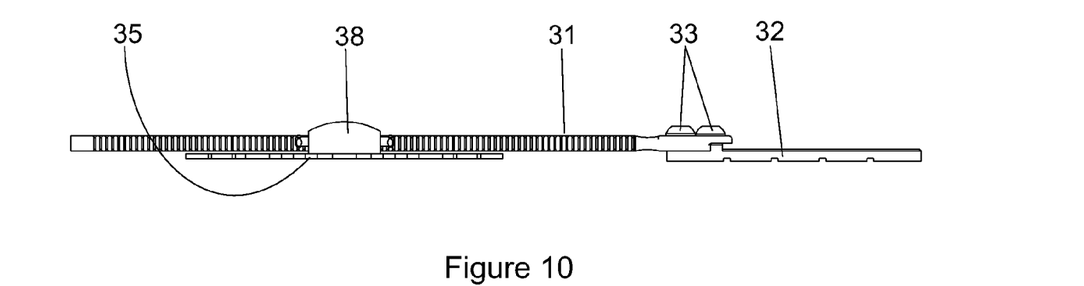
FIG. 10 is a plan view (edge on) of the apparatus illustrated in FIG. 9.

After proper planning it is relatively straightforward to secure the distractor in position on a patient during a surgical procedure using conventional fasteners, such as implantable titanium bone screws. FIG. 8 illustrates schematically the basic installation of the distractor.

The important benefit that the distractor (1) exhibits is that it can be easily used on a range of curved trajectories.

In this embodiment, the worm gear has a pitch of 1 mm, a threaded length of 6.6 mm, an outer diameter of 4.2 mm and a thread height of 0.6 mm. The toothed rack of the track has a pitch of 1 mm. The prescribed distraction rate and rhythm is 0.75 mm twice a day or 1.5 mm once a day, which, with a thread pitch of 1 mm, corresponds to one and a half turns of the worm gear per day. The patient is usually required to perform the daily distractions. In order to ensure that the healing tissue is not overstrained by more than 10%, it is assumed that patients are capable of rotating the worm gear in increments of half a turn to an accuracy of within 36°. To assist the patient, a tool (not shown) is provided, the tool being configured to indicate through a ratchet mechanism when a half turn has been completed.

The distractor is easy to assemble and use; is robust and cost effective and, most importantly, permits distraction on curved trajectories.

It will be appreciated, however, that many other embodiments of the invention exist which fall within the scope hereof, particularly regarding the configuration and shape of the track, fixation plate and carriage. For example, the gear need not be a worm gear but could, for example, be a pinion gear.

The distractor can achieve bilateral locomotion and the traction is accomplished by the worm propagating either on top of the rail or at the bottom (depending on its placement), thus providing a low profile, almost as thick as the rail itself. Due to the low profile and the design parameters the distractor of this invention can follow a spiral path and a curvature having a radius of as little as 20 mm.

Referring now to the embodiment of the invention illustrated in FIGS. 9 to 15, one of the main differences is that the track (31) is made as a separate item from a separate elongate mounting (32) and is attached to one end of the latter by means of a pair of fasteners. This arrangement has a number of advantages in that the track can be removed from a patient as may be required and he reinstalled without disturbing the secure attachment of the separate elongate mounting to the patient. Removal may take place in a direction that is transverse to the length of the track so as to enable the track to be (i) removed from a patient as may be required and (ii) reinstalled in a patient without disturbing the secure attachment of the separate elongate mounting to the patient.

Figure 11:
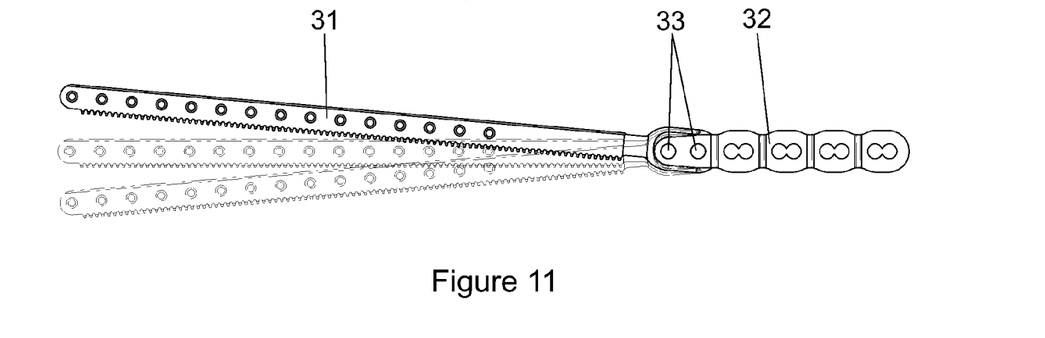
FIG. 11 illustrating elevation adjustments that can be accommodated by connection of the track to a separate elongate mounting.
Figure 12:
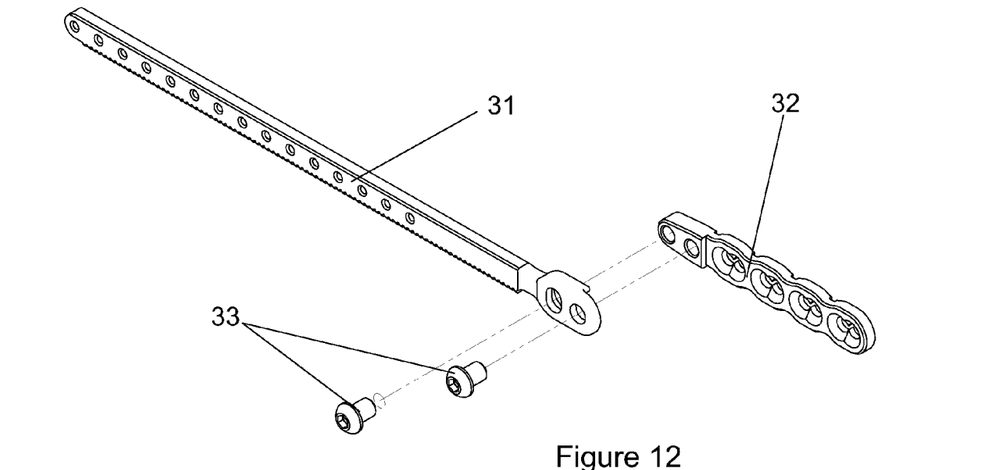
FIG. 12 illustrating perspective view the attachment of the track and separate elongate mounting of the embodiment illustrated in FIGS. 9 to 11.

Also, as shown clearly in FIG. 11, the arrangement enables the angular attachment of the track to the separate elongate mounting to be varied within certain limits that provides an advantage in orientating the various components suitably. As shown most clearly in FIG. 12, the track is secured to the separate elongate mounting using a pair of screws (33).

The use of a separate elongate mounting has an additional advantage in that it enables the track, at least in the region of attachment to the mounting, to be spaced from the bone of the patient with the advantages indicated above.

In this embodiment of the invention the fixation plate (35) has narrower arms (36) each with a single row of perforations (37) in order to provide additional flexibility for contouring the arms for attachment to a patient. A contoured set of arms is illustrated simply by way of example in FIG. 15.

Figures 13, 14:
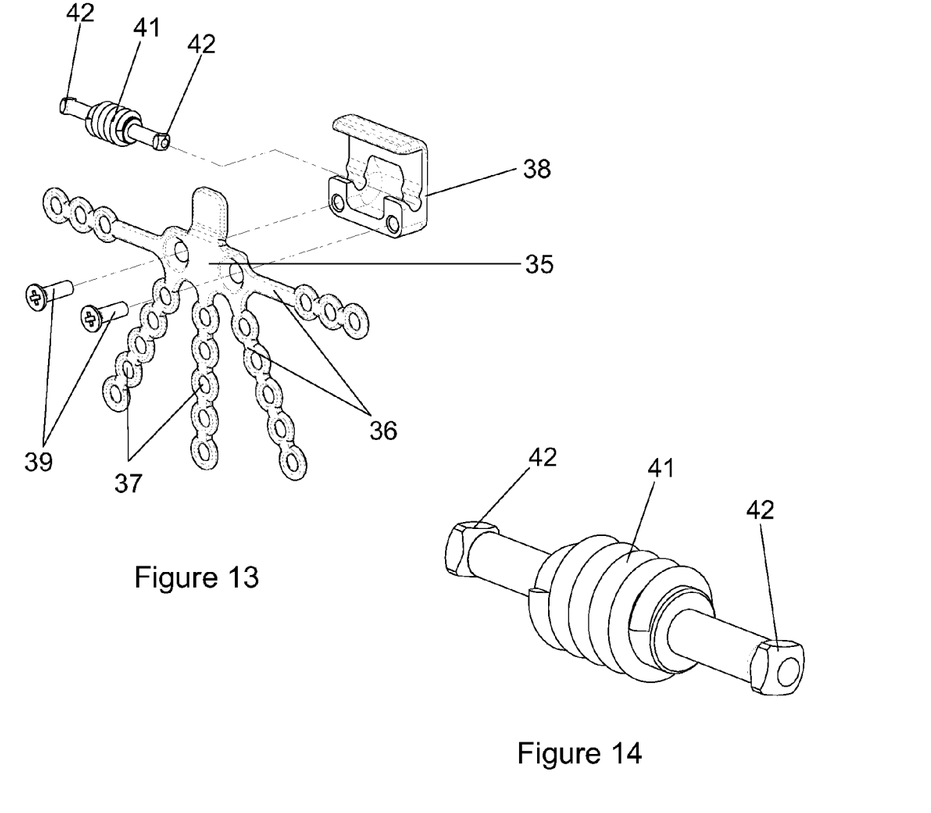
FIG. 13 is an exploded perspective view of the carriage and fixation plate of the second embodiment of the invention.
FIG. 14 is a very much enlarged perspective view of the worm gear employed in the second embodiment of the invention; and, FIG. 15 illustrates the manner in which the various components of the apparatus can be bent in order to be accommodated in a patient.

The attachment of the fixation plate to the carriage (38) is simplified in that it uses two screws (39), as shown in FIG. 13. The hook of the first embodiment of the invention is therefore omitted.

As regards the formations whereby the worm gear (41) can be rotated by a suitable socket on a tool (not shown), these assume the form of square cross-sectioned heads (42) with rounded front and rear faces such that a socket can be effectively engaged with such a head whilst not being coaxial and rotation can be achieved somewhat in the manner of a universal joint.

This embodiment of the invention therefore has a number of advantages over the embodiment described with reference to FIGS. 1 to 7.

It will be understood that numerous other variations may be made to the embodiments of the invention described above without departing from the scope hereof. Also, the different aspects of the invention may be used either individually or in any combinations of two or all of the aspects, as design considerations may dictate.

The invention claimed is:

1. A transport distraction apparatus suitable for performing transport distraction osteogenesis on the maxilla of a patient, the transport distraction apparatus comprising:
   a track having a rectangular cross-section with a width greater than its thickness to provide a front and a rear face and two longitudinally extending edges one of which has a toothed rack extending along its length and wherein the track is capable of being formed into a curvilinear shape with a curvature radius suitable for accommodation in the maxilla of a patient;
   a carriage movable longitudinally along the track and to which a fixation plate is releasably secured, the fixation plate (i) including a hook-shaped attachment formation configured to fit over an edge of the carriage and (ii) configured to extend between the track and a bone of a patient and wherein the carriage includes a first side and a second side, the second side extending in a direction transverse to the first side, and wherein the hook-shaped attachment formation engages the first and second sides; and
   a worm gear having a helically extending thread which meshes the toothed rack extending along one edge of the track for moving the carriage along the track in order to adjust its position relative to the length of the track, wherein the worm gear is at least partially accommodated within a space between a plane including the front face of the track and a plane including the rear face of the track, and wherein the track itself is made as a separate item from a separate elongate mounting and one end of the track is releasably secured by first fasteners to the separate elongate mounting that is securable by second fasteners to bone in a patient and wherein the first fasteners, track, and separate elongate mounting are configured to enable the track to be removed from the separate elongate mounting in a direction that is transverse to the length of the track so as to enable the track to be (i) removed from a patient as may be required and (ii) reinstalled in a patient without disturbing the secure attachment of the separate elongate mounting to the patient.

2. A transport distraction apparatus as set forth in claim 1, wherein the worm gear has formations at both ends thereof for releasable engagement by a tool for rotating the worm gear and thereby moving the carriage relative to the length of the track.

3. A transport distraction apparatus as set forth in claim 1, wherein the mounting or shaping of the track is such that a central region of the track and the attachment or attachment position for the fixation plate to the carriage are spaced forwardly of the separate elongate mounting that is configured to be operatively secured to bone in a patient.

4. A transport distraction apparatus as set forth in claim 3, wherein the rear face of the central region of the track is spaced forwardly of a rear face of the separate elongate mounting that is configured to be operatively secured to bone in a patient by a distance of the order of the thickness of the elongate mounting.

5. A transport distraction apparatus as set forth in claim 1, wherein the fixation plate is a generally flat plate having the hook-shaped attachment formation attaching the plate to the carriage, and wherein the fixation plate has deep generally sector shaped cut-out portions extending inwardly towards the attachment formation so as to define plural arms capable of independent bending to conform generally to a three-dimensional curve.

6. A transport distraction apparatus as set forth in claim 5, wherein the fixation plate is generally semicircular in shape with two, three, or four sector shaped cut-out portions defining a plurality of arms extending in a generally radial direction from the attachment formation.

7. A transport distraction apparatus as set forth in claim 6, wherein each of the arms is perforated with multiple perforations that can be used for securing the fixation plate in position, in use.

8. A transport distraction apparatus as set forth in claim 1, wherein the track is angularly adjustable relative to the separate elongate mounting.

9. A transport distraction apparatus as set forth in claim 1, wherein the track includes a titanium material configured to be formed into the curvilinear shape.

10. A transport distraction apparatus as set forth in claim 1, wherein the track includes a first end and a second end opposite the first end, the first end releasably secured to the separate elongate mounting by the first fasteners, and the second end being devoid of fasteners.

11. A transport distraction apparatus as set forth in claim 1, wherein the fixation plate and the hook-shaped attachment formation collectively define a U-shape.

* * * * *